US006364914B1

(12) United States Patent
Ueda et al.

(10) Patent No.: US 6,364,914 B1
(45) Date of Patent: Apr. 2, 2002

(54) METHOD OF CRYSTALLIZATION WITH THE PARTICLE SIZE DISTRIBUTION BEING CONTROLLED

(75) Inventors: Hiroshi Ueda; Hiroshi Fukushi; Muneyuki Ozawa, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/272,405

(22) Filed: Mar. 19, 1999

(30) Foreign Application Priority Data

Mar. 23, 1998 (JP) .......................................... 10-073948

(51) Int. Cl.[7] .......................... B01D 9/00; C30B 17/00; C07C 7/00; C07C 7/14; C07C 229/00

(52) U.S. Cl. ......................... 23/295 R; 23/296; 23/301; 585/800; 585/812; 585/813; 562/562; 562/561

(58) Field of Search .............................. 23/295 R, 301, 23/296; 585/800, 812, 813; 562/562, 561

(56) References Cited

U.S. PATENT DOCUMENTS 3,634,043 A * 1/1972 Laurich .................... 23/295 R
4,263,011 A * 4/1981 Huguenard et al. ........... 23/300
5,194,625 A * 3/1993 Tanabe et al. .............. 548/544
5,240,467 A * 8/1993 Johnson ....................... 23/296
5,571,301 A * 11/1996 Yamaura et al. .............. 65/335

FOREIGN PATENT DOCUMENTS

| | | |
|---|---|---|
| DE | 2 353 979 | 5/1974 |
| EP | 0 139 573 | 5/1985 |
| NL | 7707345 | 7/1977 |

OTHER PUBLICATIONS

Perry, John, H. "Crystallization Apparatus". Chemical Engineers' Handbook, pp. 1065–1068, 1950.*
English language abstract of NL 7707345, Jan. 1978.*
Patent Abstracts of Japan, vol. 012, No. 128 (C–489), Apr. 20, 1988, JP 62–247802, Oct. 28, 1987.

* cited by examiner

*Primary Examiner*—Steven P. Griffin
*Assistant Examiner*—Jonas N. Strickland
(74) *Attorney, Agent, or Firm*—Oblon, Spivak, McClelland, Maier & Neustadt, P.C.

(57) ABSTRACT

Herein is disclosed a method of crystallization with the particle size distribution being controlled, characterized in that while crystals are being precipitated by vacuum concentration crystallization, the temperature of the slurry is periodically varied up and down during the concentration of the crystallization mother liquor (i.e., the slurry), which method is an excellent one free from the defects of the conventional methods.

15 Claims, 11 Drawing Sheets

(50-60°C TEMP. SWING) (KEPT AT 50°C)

(a) INVENTIVE (b) CONTROL

LOT (1) (CONVENTIONAL)

LOT (2) (INVENTIVE)

METHOD OF CRYSTALLIZATION WITH THE PARTICLE SIZE DISTRIBUTION BEING CONTROLLED

BACKGROUND OF THE INVENTION

1. Field of the Invention

The present invention relates to a method of crystallization through vacuum concentration. More specifically, it relates to a method of crystallization through vacuum concentration in which crystals having a uniform particle size within a narrow particle size distribution range can be obtained by periodically varying up and down or swing the temperature of the slurry (mass temperature) during concentration of the slurry (i.e., the crystallization mother liquor) from which crystals are to be precipitated.

2. Background Art

A method of crystallization by controlling the particle size distribution (i.e., with the particle size distribution being controlled) in which crystals having a uniform particle size in a narrow particle size distribution range can be obtained is useful in, for example, the following fields, and the development of an excellent method of crystallization by controlling the particle size distribution has been in high demand. The said following fields are as follows;

(1) When a crystal product has to comply with a particle size standard, the crystallization is controlled in such that the particle size of crystals precipitated is arranged within the standard, whereby the yield (i.e., the standard pass rate) of the product is improved.

(2) The crystallization is controlled in such that formation of fine crystals is suppressed, whereby the solid-liquid separability of the crystals precipitated is improved and the purity thereof is, in turn, increased (by decreasing the mother liquor adhering thereto).

(3) Likewise, the separability is improved to reduce the time required for separation, which, in turn, improves the productivity.

(4) When the solid-liquid separation using a cloth filter is repeated, a dense bed layer remains on the filter cloth, so that the separability is gradually decreased. Accordingly, the separability has to be restored through washing or the like. At this time, however, the content moved into the washings becomes a loss. If the crystal separability gets better, this loss is reduced, and the yield is increased, contributing to the improvement of the productivity.

In this connection, as the method of crystallization by controlling the particle size distribution, or with the particle size distribution being controlled, for example, the following methods have been so far proposed.

(a) Method described in JP-B-49-29,821:

This relates to a method in which the alumina content is extracted from an aluminous mineral through treatment with sulfuric acid, and aluminum sulfate is produced as high-quality crystals from the extract. Specifically, it is a method of producing aluminum sulfate, comprising, in combination, a first step of precipitating aluminum sulfate crystals by cooling a part of a sulfuric acid-acidic aluminum sulfate solution of a high temperature which has been obtained by treating an aluminous mineral with sulfuric acid, a second step of increasing the temperature of the solution in which the aluminum sulfate crystals have been precipitated to such an extent that the crystals therein are partially dissolved, maintaining this temperature for a predetermined period of time, then recooling the solution to precipitate additional aluminum sulfate crystals, and repeating this procedure to obtain hexagonal plate crystals, and a third step of adding the resulting hexagonal plate crystals to the saturated or nearly saturated sulfuric acid-acidic solution which is the residual portion of the aluminum sulfate solution obtained in the first step to precipitate the aluminum sulfate hexagonal plate crystals and separate the same.

It is further stated that according to this method, there is no need to select an aluminous ore having a high alumina content, crystals of aluminum sulfate formed are thick hexagonal plate crystals having a good filterability, and impurities adhering to the crystals can be easily removed through washing.

(b) Method described in JP-A-62-247,802:

This relates to a batchwise cooling crystallization method (i.e., a batchwise method of crystallization by cooling), and more specifically to a method in which coarser crystals are obtained. Specifically, it is a batchwise cooling crystallization method characterized in that after cooling starts and a part of the solute is crystallized, cooling is stopped, and heating is conducted; and before the crystals precipitated are completely dissolved, the heating is stopped, and recooling is conducted.

The reasons for proposing such a method are described as follows. In the batchwise cooling crystallization, the conventional method employed to increase the crystal size includes adjustment of cooling rate, adjustment of solute concentration, adjustment of solute composition, and the like.

Further, crystallization medium is some times studied. However, in case that upon studying these methods the improvements are not expected or it is difficult to change the composition and the concentration in view of the process and there is no room for investigation, the production might be impossible, but this inventive method is a simple, quite useful crystallization method upon solving the problems.

(c) Method described in JP-A-5-111,602

This relates to a method of forming crystal particles having a uniform particle size, which method is required for production of sugar and the like, and more specifically to a method of crystallizing crystal particles from a solution, which comprises conducting crystallization in a crystallizer, while measuring the particle size distribution of the crystal particles with a particle size meter fitted in the crystallizer, and decreasing the degree of saturation of the solution based on the detection when detecting that the number of particles in the particle size distribution exceeds a predetermined value.

The reasons for proposing such a method are described as follows. That is, for example, in the conventional sugar crystallization method, it was difficult to obtain crystal particles having a uniform particle size at good efficiency. That is, in order to shorten a crystallization time, a growth rate of crystal particles can be increased by increasing the degree of supersaturation of a solution. However, when the degree of supersaturation of the solution is increased too much, mimetic crystals, i.e., crystal nuclei newly formed besides the seed crystals, are generated to make non-uniform the particle size of the crystal particles. In order to remove the mimetic crystals formed, a solvent is added to the solution to reduce the degree of supersaturation, making it possible to remove the mimetic crystals by dissolving. However, when such re-dissolution is conducted after the mimetic crystals are grown, the time for re-dissolution is required, and the desired crystal particles are also dissolved. Accordingly, the overall crystallization time is increased to make impossible the efficient production. Therefore, for obtaining crystal particles having a uniform particle size, it is important that while observing the condition of the crystallization, a solvent and a solution are added or removed to control the solution to an optimum degree of supersaturation. The crystallization has been so far conducted based on the visual observation and the experiences of workers. Or, the degree of supersaturation has been controlled for automation, by measuring the viscosity correlated with the density and the particle size of crystal particles using a densitometer. However, such controlling is problematic in that the reproducibility in the crystallization step is poor. Incidentally, the particle size of the crystal particles in the solution within a crystallizer cannot accurately be measured with the conventional particle size meter with which the precipitation rate of the particles is measured. This is because when the solution and the crystal particles are withdrawn from the crystallizer for the measurement, the temperature and the like are changed to change the degree of supersaturation, so that the dissolution and the growth of the crystal particles occur. Meanwhile, the inventive method has dissolved such problems, and it aims to provide a crystallization method in which crystal particles having a uniform particle size can be obtained with good reproducibility (refer to paragraphs [0003] to [0007] of the same document).

Nevertheless, such a method of crystallization by controlling the particle size distribution as proposed so far still involves various problems (to be described later), and the further improvement has been in demand.

SUMMARY OF THE INVENTION

In view of the background of such conventional techniques, it is one object of the present invention to provide an excellent method of crystallization by controlling the particle size distribution i.e., with the particle size distribution being controlled, which method is free from the defects of the conventional methods.

The present inventors have assiduously conducted investigations to achieve the and other objects, and have consequently found that while the crystallization mother liquor is concentrated to precipitate crystals, the temperature of the slurry, i,e., the mother liquor, (mass temperature) is periodically varied up and down during the concentration whereby crystals having a uniform particle size in a narrow particle size distribution can be obtained. These findings have led to the completion of the present invention.

That is, the present invention relates to a method of crystallization with the particle size distribution being controlled, i.e., while controlling the particle size distribution, characterized in that while crystals are being precipitated through crystallization by vacuum concentration, the temperature of the slurry is periodically varied up and down during the concentration of the crystallization mother liquor, i.e., the said slurry.

DETAILED DESCRIPTION OF THE PREFERRED EMBODIMENTS

Figure 1:
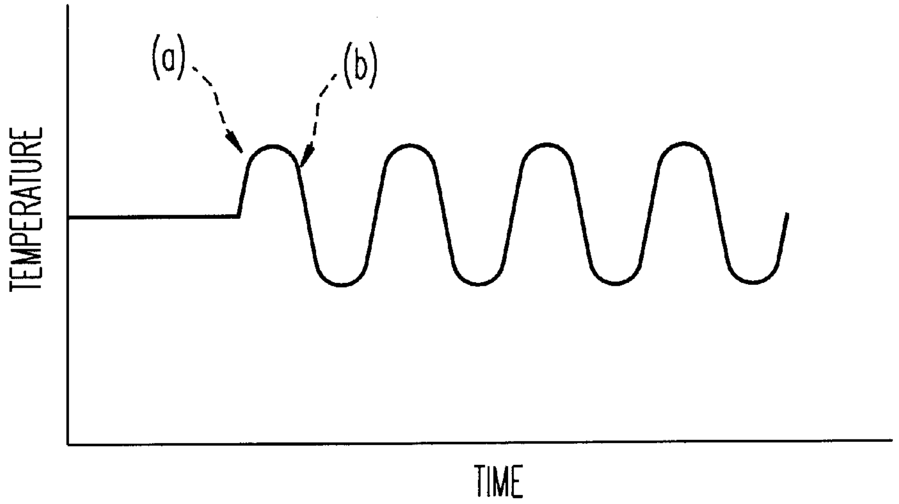
FIG. 1 indicates a temperature pattern in the temperature-swung procedure.

The present invention will be described in detail below.

A crystallization method in which a certain substance is crystallized from a solution of the substance includes, for example, a concentration crystallization method, a cooling crystallization method, and the like, as is well known. The method of crystallization by controlling the particle size distribution (i.e., with the particle size distribution being controlled) of the present invention belongs to the concentration crystallization method.

The concentration crystallization method is roughly classified into two categories, i.e., one is a method in which crystallization is conducted under atmospheric pressure in an open system, and the other is a method of crystallization which is conducted under reduced pressure using a vacuum concentration crystallizer, this method being called vacuum concentration crystallization. The crystallization method of the present invention is limited to vacuum concentration crystallization in view of the temperature control when the crystallization is conducted upon periodically varying up and down the temperature of the slurry (mass temperature). This is because in an open system under atmospheric pressure, a boiling point is determined by the atmospheric pressure, making it impossible to optionally vary the temperature. Since the temperature of the slurry is periodically varied up and down during the concentration of the crystallization mother liquor or the slurry according to the concentration crystallization method of the present invention as has been described above, this is at times abbreviated as a "temperature-swung (concentration) crystallization method". Further, the procedure of periodically varying up and down (i.e., swinging) the temperature is at times abbreviated as a "temperature-swung procedure".

The concentration crystallization method is usually conducted at a fixed temperature because of its nature, so that the slurry, i.e., the crystallization mother liquor, has a fixed temperature. According to the crystallization method of the present invention, the temperature is periodically varied up and down within a fixed range (delimited by the upper limit and the lower limit), and therefore, from the macroscopic point of view, it can be said that the crystallization of the present invention is conducted at a fixed temperature. Further, the concentration crystallization can be conducted in a continuous manner, a batch manner or a fed-batch manner which is said to be an intermediate manner between the first two manners (the last-mentioned manner is one in which concentration crystallization is continuously conducted for a certain period of time, and then stopped, after which the whole slurry in the crystallizer is discharged, and the next, crystallization procedure is newly started). These manners are distinguished based on the different feeding manners of the crystallization mother liquor (on which the manner of discharging the crystals precipitated depends). The concentration crystallization of the present invention can be conducted in any of these manners.

According to the temperature-swung crystallization method of the present invention, the temperature within the concentrator (slurry temperature) is periodically varied up and down during the concentration crystallization. A temperature pattern of this temperature-swung procedure is shown in FIG. 1. In FIG. 1, (a) is a course of temperature rise, and (b), a course of temperature drop (cooling).

The temperature can be easily swung or varied periodically up and down in a vacuum concentrator by adjusting the pressure with an exhaust line valve.

Dissolution and precipitation are repeated in the vacuum concentrator by swinging the temperature. The relationship between the slurry concentration and the solubility at this time is shown in FIG. 2.

Figure 2:
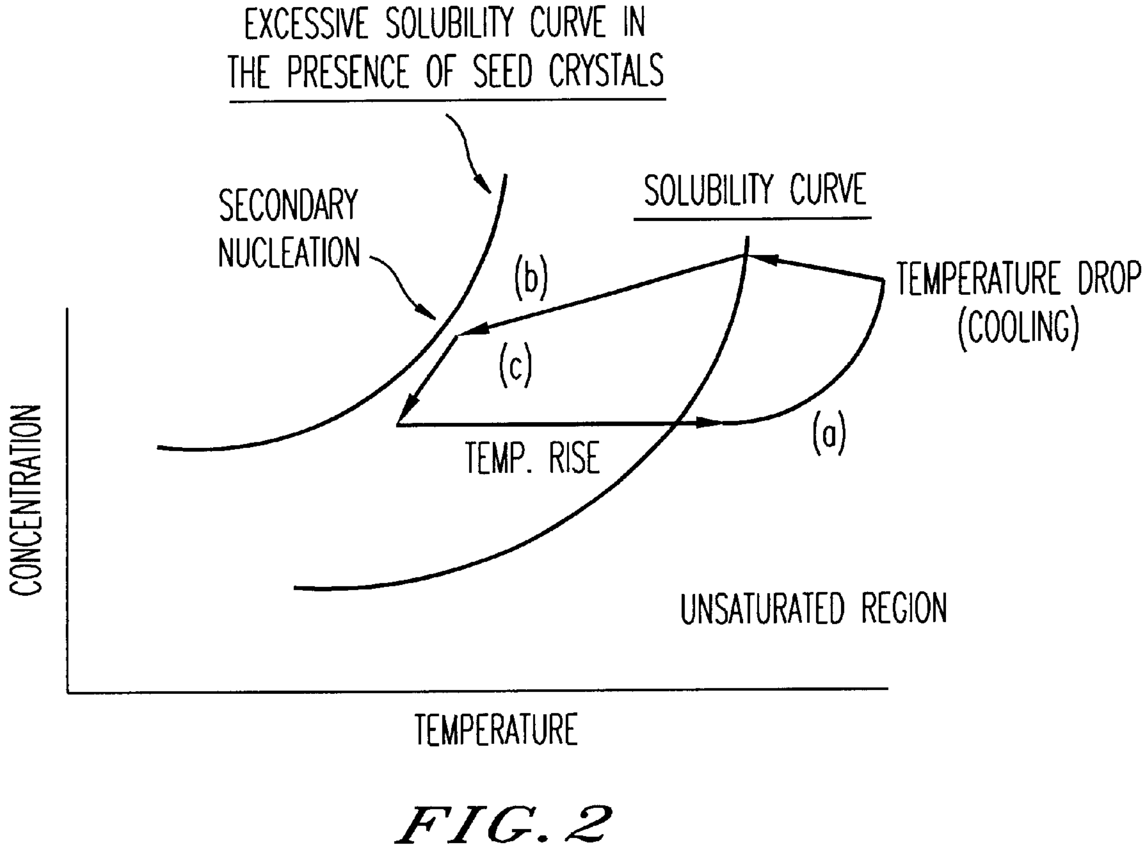
FIG. 2 indicates the relationship between the slurry concentration and the solubility in the temperature-swung method.

In FIG. 2, (1) when the increment in the solubility at the time of the temperature rise (course (a)) exceeds the increment in the concentration by the introduction of the concentrate feed solution (crystallization mother liquor), an unsaturated state is provided, and a part of the slurry crystals are dissolved. At this time, fine crystals are more rapidly dissolved and disappear owing to the smaller weight and surface area. (2) When the liquid concentration of the slurry exceeds the solubility through the cooling (course (b)), the crystal growth starts depending on the degree of supersaturation. As the cooling proceeds and the degree of supersaturation increases, the crystal growth rate increases. At this time, since the liquid concentration of the slurry is in a metastable supersaturation region, almost no secondary nucleation occurs spontaneously. (3) When the degree of supersaturation further increases through the cooling and the concentration (course (c)), the secondary nucleation occurs. When this cycle is repeated, the dissolution of fine crystals and the crystal growth in the metastable supersaturation region occur. As a result, the fine crystals are decreased by an amount of the fine crystals dissolved in (1) minus the fine crystals resulting from the secondary nucleation in (3). Such is a principle in accordance with which the particle size distribution is controlled by the temperature-swung crystallization method of the present invention.

As the factors that influence the particle size distribution of crystals in the temperature-swung crystallization method of the present invention, there may be mentioned the range of the change in the temperature (swung range or amplitude) and the period. For example, with respect to the temperature rise, at least the increase in the solubility has to occur faster than the increase in the (supersaturated) concentration through the ordinary concentrating procedure. Further, the period or the swung range of the change in the temperature can be determined in a range adaptable to a desired particle size distribution depending on the feed rate (namely, the concentrating rate) of the substance. When the factors are adjusted in this manner, it is possible to conduct the crystallization with the particle size distribution being controlled using even an ordinary simple batch-type vacuum concentrator.

Since the temperature-swung crystallization method of the present invention enables the crystallization with the particle size distribution being controlled upon only adding the temperature swing to the temperature control in the simple vacuum concentrator without the need for an additional equipment and without the change in the operation conditions such as prolongation of a concentration time. Thus, it finds extremely wide application, and is quite practical.

The crystallization method of the present invention is especially effective for the crystallization of substances having a high dependence of their solubility on temperature.

The main points of the temperature-swung crystallization method of the present invention have been described above. Next, in order to facilitate the understanding of the temperature-swung crystallization method of the present invention, (1) special characteristics of the temperature swing, (2) special characteristics of the temperature swing in the concentration crystallization, (3) the cooling temperature swing and the concentration temperature swing, and (4) the determination and the control of conditions for conducting the temperature-swung crystallization method will be described.

(1) Special characteristics of the temperature swing:

In the ordinary vacuum concentration crystallization, the slurry temperature (pressure) is fixed for the following reasons (incidentally, in the vacuum concentration crystallization, a certain inner pressure (atmospheric pressure) corresponds to the specific temperature (slurry temperature) and vice versa). That is, (a) a fixed inner pressure tends to keep a fixed supersaturation of the slurry. Generally, a procedure that is likely to cause a rapid increment in supersaturation should be avoided because fine crystals tend to occur. (b) The rapid change (decrease) in the pressure is likely to cause a loss due to bumping. (c) When the concentration (evaporation) is conducted at a lower temperature (lower pressure), an energy efficiency is generally better. Accordingly, it is usually conducted at the lowest possible pressure of a device using a vacuum pump, providing an air tightness, and the like, whereby the operation is consequently conducted at a nearly constant pressure.

(2) Special characteristics of the temperature swing in the concentration crystallization:

(a) In order to positively swing, or vary up and down, the temperature, a special control is required (in the instrumental aspect), in comparison with the control at a fixed pressure and temperature. However, in the method of the present invention, such control can be conducted quite easily.

(b) It is usually unavoidable that fine crystals are formed during the concentration. In the concentration temperature swing, the swing is repeated during the concentration to continuously decrease the fine crystals. Further, in the temperature swing, there is a likelihood that the supersaturation greater than that by the concentration crystallization at a constant temperature occurs during the temperature drop and it may expedite formation of fine crystals. In the temperature-swung method, the temperature is raised before a vigorous nucleation occurs, upon utilizing the waiting time in the nucleation of crystals, to suppress the increment of fine crystals (re-dissolution is conducted before the stable growth of crystal nuclei).

(c) When it is required that fine crystals disappear, a crystallizer having a performance of separately dissolving fine crystals alone, such as a DTB crystallizer, is used in the existing technique. When the temperature swing is introduced, there are advantages that the apparatus becomes simple without adding such an intricate device, sanitariness is improved, a loss in washing and recovery is decreased, and the like. These are especially advantageous for the batch crystallization of drugs.

(3) Differences between the cooling temperature swing and the concentration temperature swing:

Since the temperature is repeatedly raised during the crystallization in the cooling temperature swing, excess energy is required in comparison with the ordinary cooling crystallization. Consequently, there are demerits that the crystallization time gets longer and the productivity is lowered. Meanwhile, in the vacuum concentration temperature swing, almost no excess energy is required in comparison with the ordinary vacuum concentration crystallization, and fine crystals can be allowed to disappear without prolonging the crystallization time. Thus, there are almost no demerits.

The vacuum concentration temperature swing is almost free from the demerits encountered in the cooling temperature swing will be described as follows. That is, the concentration time required corresponds to the difference in the total energy consumption when a heat introduction rate is fixed. The total energy consumption is, in turn, (total inner energy at the termination of the concentration)−(total inner energy at the start-up of the concentration). If the temperature is 50° C. in the start-up of the concentration both in the case of conducting the temperature swing (50 to 60° C.) and in the case of not conducting the same, the difference in energy consumption becomes the difference in energy at the time of the termination of the concentration. When the concentration is terminated, the system is in the state of the slurry and the water vapor. If the respective liquid parts of the slurries is in the same condition in both cases, the difference therebetween is a difference in the condition of the water vapor at the termination of the concentration. The volume of the water vapor is the same in both cases. However, when the swing is not conducted, the temperature of the water vapor is 50° C. Meanwhile, when the swing is conducted, it is approximately 55° C. Strictly speaking, excess energy is consumed by this difference in case the of conducting the swing. If the swing is not conducted, an energy of heat of evaporation of 569 cal/g is required at 50° C. On the other hand, when the swing is conducted, an energy is consumed more by approximately 2 cal/g required for heating the water vapor of 50° C. to that of 55° C. This difference is an actually negligible difference. Accordingly, the concentration time and the energy consumption are nearly equal both in case of conducting the temperature swing and in case of not conducting the temperature swing.

(4) Determination and control of the conditions for conducting the temperature-swung crystallization:

(a) In the vacuum crystallization, an in-crystallizer pressure (degree of vacuum) corresponds to the specific concentration temperature (slurry temperature) and vice versa. The crystallizer inner pressure (i.e., in-crystallizer pressure) is varied up and down (by adjusting an exhaust valve) simultaneously with the concentration crystallization, whereby the temperature swing is caused and the crystals in the slurry are dissolved or precipitated. The pressure is adjusted continuously by directly monitoring the pressure or the temperature so as not to abruptly change the same. If the pressure is abruptly decreased, there is a risk that bumping might occur.

(b) For temporarily dissolving the slurry, the temperature has to be elevated at a higher rate than the concentration is increased through the concentration. The temperature has to be raised until the unsaturated condition is reached from the supersaturated condition. Whether the unsaturated condition is reached or not can be identified by the fact that the rate of the increase in the concentration of the liquid part exceeds the increase in the concentration through the concentration (crystals are dissolved). The rate of the increase in the concentration of the liquid part can be observed by monitoring the refractive index in the concentrator for substances of which the concentration is correlated with the refractive index, such as amino acids and sugar solutions.

(c) In the cooling (decrease in the pressure), in order to minimize the occurrence of fine crystals resulting from the cooling, it is required that the slurry is cooled as rapidly as possible before the nucleation is stabilized, in consideration of the nucleation waiting time of the crystallization and is moved to the step of raising the temperature. Furthermore, for increasing the effect in the subsequent step of raising the temperature, the liquid concentration is lowered nearly to the solubility when the cooling is terminated. In the determination of the cooling (decrease in the pressure) condition, as high a cooling (decrease in the pressure) rate as possible is selected at such that the concentration is lowered nearly to the solubility at the termination of the cooling, by monitoring the change in the liquid concentration with a refractive index or the like.

(d) The temperature range is determined by obtaining the conditions for dissolving a solute in an amount corresponding to that of the crystals of a particle size required to disappear, from the increment in the refractive index when raising the temperature.

(e) The determination of these conditions can be conducted quite easily by those skilled in the art using an actual production equipment or by a simulation test in a laboratory or a bench plant.

Finally, the crystallization methods described in the patent documents of the prior-art techniques quoted earlier are compared with the crystallization method of the present invention, which would facilitate the understanding of the crystallization method of the present invention.

(a) In the method of producing aluminum sulfate as described in JP-B-49-29,821, only the production of seed crystals from the crystallization mother liquor is conducted by the temperature-swung procedure (first and second steps). Most of the desired final substance remaining after the seed crystals are precipitated by a method other than the temperature-swung procedure. This cannot realize the effects of the method of crystallization with the particle size distribution being controlled, though using the temperature swing according to the present invention where all of the desired substance is precipitated by the temperature-swung crystallization. Further, the method described in this document is the cooling crystallization, which is basically different from the vacuum concentration temperature-swung crystallization of the present invention.

(b) The crystallization method described in JP-A-62-247, 802 is a batchwise cooling crystallization method. The point of this method is to obtain coarse crystals through the cooling crystallization. Only fine crystals, among the crystals formed through spontaneous crystallization, are dissolved by raising the temperature (temperature swing) during the cooling step to give seed crystals. This cannot cope with the secondary nucleation in the course of the crystallization procedure. On the other hand, the crystallization method of the present invention is a concentration crystallization method, and it aims to remove the fine crystals formed through the unavoidable continuous secondary nucleation in the course of the concentration crystallization. It is different-from the crystallization method described in the above-mentioned patent document with respect to the object and the procedure. In addition, as stated above, there is almost no difference in the energy required between the case of conducting the temperature swing in the vacuum concentration crystallization method of the present invention and the case of not conducting the temperature swing in the conventional vacuum concentration crystallization method. However, in the cooling crystallization method, the energy required becomes higher in case of conducting the temperature swing than in case of not conducting the same.

(c) The method described in JP-A-5-111,602 is characterized in that the secondary crystallization is discovered at an early stage and crystals formed therein are dissolved to disappear with the addition of a solvent. This method has such demerits that the energy required is increased and the concentration time is prolonged because of the increase in the amount of the solvent. On the contrary, according to the temperature-swung method of the present invention, the temperature swing can be realized only by actuating an exhaust valve during the concentration, with the result that no such demerits are provided. Further, it has been known that fine crystals disappear (are dissolved) by heating. When the temperature swing is conducted, great supersaturation occurs at the time of the temperature drop to form fine crystals. However, according to the temperature-swung method, this problem is solved by periodically conducting the temperature swing continuously and adjusting the swing range.

EXAMPLES

The invention will be illustrated more specifically by referring to Experiment Example 1 and Example 1

Experiment Example 1

Influence of the temperature swing on the crystal particle size:

(1) Purpose of the experiment:

This experiment was conducted to identify the change in the particle size distribution of crystals by conducting the temperature swing during the concentration in the concentration crystallization of L-arginine hydrochloride (Arg.HCl) and to examine the influence of the change in some factors of the temperature swing on the crystal particle size distribution.

Figure 3:
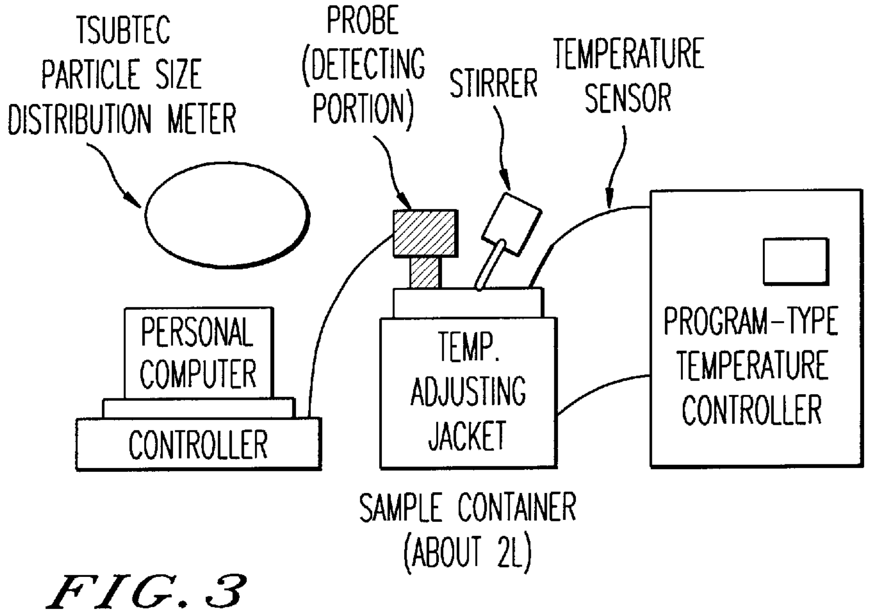
FIG. 3 indicates an apparatus for measuring the effects of the temperature swing (Experiment Example 1).

(2) Method of the experiment:

An apparatus shown in FIG. 3 was used, and the temperature swing was applied to a slurry. The particle size distribution and the change in the number of crystal nuclei owing to the temperature swing were examined.

With respect to the stirring conditions, the rotation was conducted at 200 rpm using a stirring blade having a rotational radius of 2 cm and a height of 1 cm. The number of particles and the particle size distribution were monitored using a "TSUBTEC" supplied by Laser Sensor Technology. The data of the particle size distribution was obtained by using a sphere volume calculation device attached to the "TSUBTEC".

Figure 4:
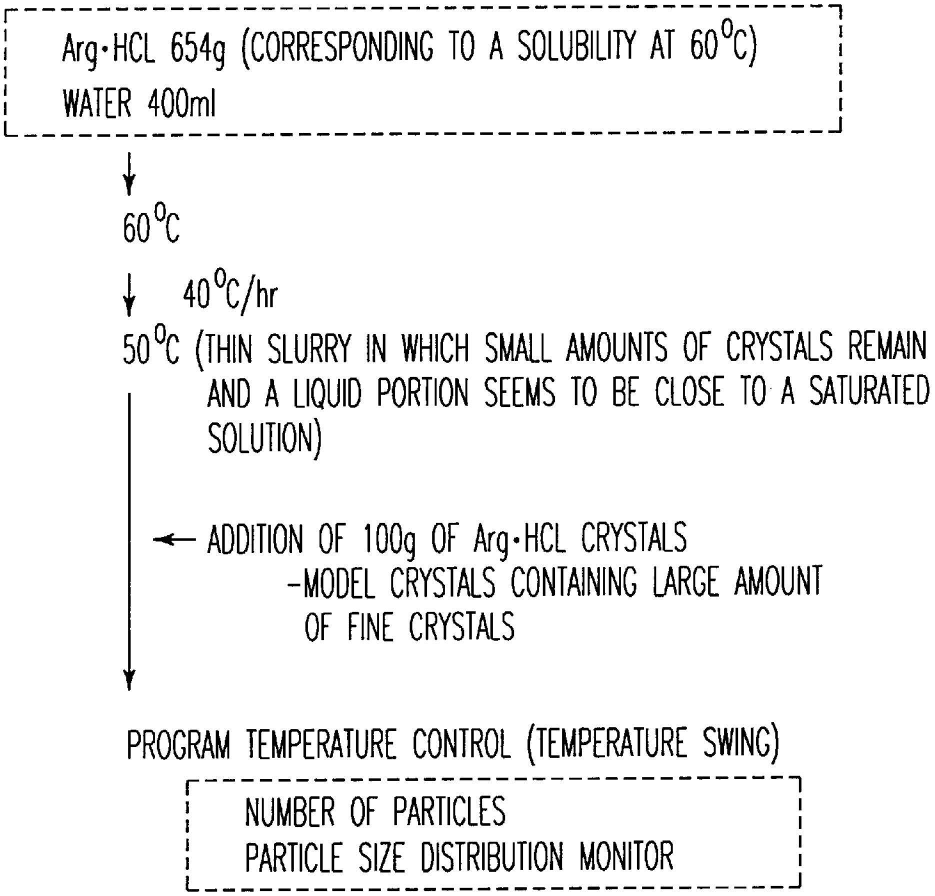
FIG. 4 indicates an Experiment flow sheet (Experiment Example 1).

As the experiment flow sheet, a flow sheet shown in FIG. 4 was established. That is, model crystals to be described later were charged into a saturated solution of 50° C., and a temperature swing was applied by a program temperature control. As a solution in which the crystals are charged, a completely saturated solution or a slightly supersaturated solution is preferable so as not to dissolve the crystals charged. Here, as a solution close to a saturated solution, a thin slurry was used which has been obtained in such manner that crystals in an amount corresponding to saturation at 60° C. were dissolved at 60° C. and cooled to 50° C. The liquid part of this slurry was considered close to the saturated (slightly supersaturated) solution.

Figure 5:
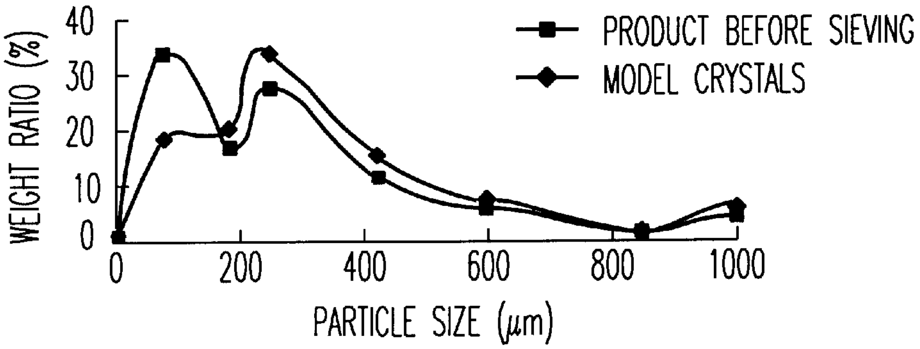
FIG. 5 indicates particle size distributions of crystals (Experiment Example 1).

The model crystals here referred to were a mixture of 80 parts by weight of an Arg.HCl product in a certain lot before sieving and 20 parts by weight of crystals of the same product passing a sieve of 125 μm or less (fine crystals). The particle size distributions of the product before sieving and the model crystals containing a large amount of fine crystals as measured with a "ROBOT SHIFTER" supplied by Seishin Kigyo are shown in FIG. 5.

The temperature swing was conducted in different five patterns (Nos. 1 to 5) for control shown in Table 1.

TABLE 1

| No. | Program | ΔC | Remarks |
|---|---|---|---|
| 1 | 50° C.→60° C.→50° C. is repeated every 30 minutes | 16 g/100 g $H_2O$ | |
| 2 | 50° C.→65° C.→50° C. is repeated every 30 minutes | 27 g/100 g $H_2O$ | |
| 3 | The cooling in No. 1 is conducted for 30 minutes (same temperature range) | 16 g/100 g $H_2O$ | Low cooling rate in No. 1 |
| 4 | Fixed at 50° C. | 0 g/100 g $H_2O$ | Control |
| 5 | Fixed after heating to 60° C. (crystals are charged at 60° C.) | 0 g/100 g $H_2O$ | Control |

ΔC: Amount of crystals dissolved (3) Results and discussion:

The temperature (swing) patterns (measured within the container) and the change in the number of crystals with time are shown in FIGS. 6A, 7A, 9A, 10A and 11A. Further, the particle size distributions (changes in the particle size distributions with time) at (a) to (d) shown in these drawings are shown in FIGS. 6B, 7B, 9B, 10B and 11B.

Incidentally, as for the "TSUBTEC", the count number (absolute number) changes depending on the stirring conditions, the position of the probe (detecting member) and the like. Under the conditions of this experiment, the number of particles was unstable, and increased for from 5 to 10 minutes at the initial stage after charging crystals owing to loosening of crystalline lumps and slight nucleation, and the like. Accordingly, the number of crystals at the peak of the initial increase in the number of particles was defined as 1, and the relative count number was indicated on the basis of this.

Figure 6A:
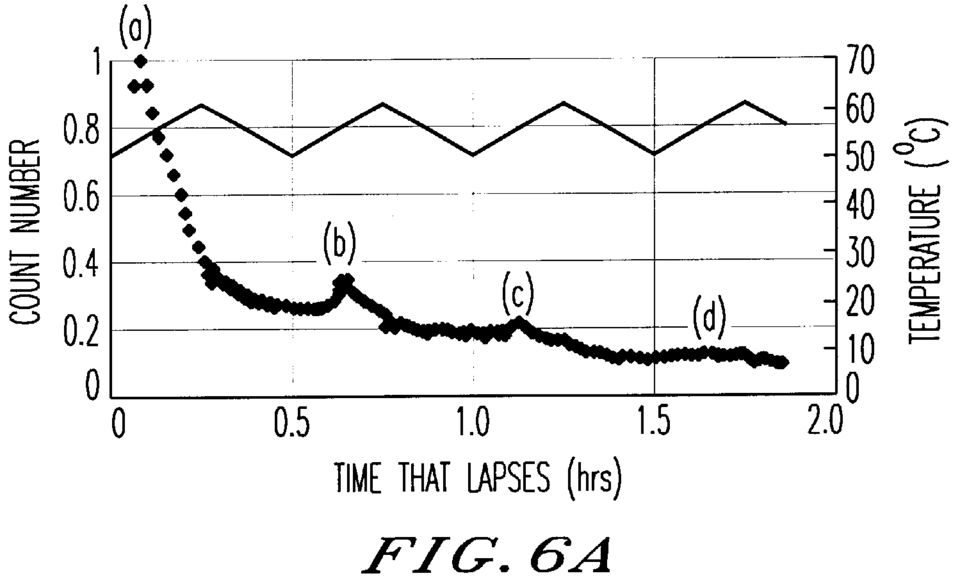
FIG. 6A indicates the change in the number of particles with time under the No. 1 condition (Experiment Example 1).

(a) Temperature pattern No. 1:

FIG. 6A reveals that the number of particles was decreased by the temperature rise, and that after the stable condition of particles during the cooling, the number of particles was slightly increased through the secondary nucleation. The secondary nucleation was decreased whenever the temperature swing was repeated. This is presumably because the ratio of fine crystals having a higher dissolution rate is decreased through the temperature swing and the ratio of crystals dissolved is decreased at every swing.

Figure 6B:
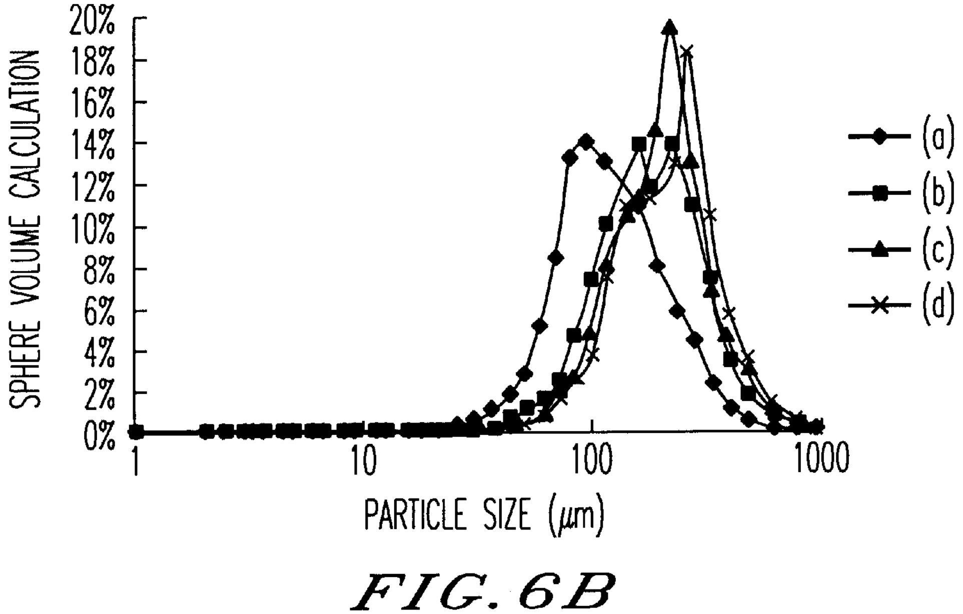
FIG. 6B indicates the change in the particle size distribution with time under the No. 1 condition (Experiment Example 1).

In FIG. 6B, the peak of the temperature swing is not consistent with the valley of the number of particles. This is presumably because the saturated solubility was not reached at the termination of the temperature rise and the dissolution still proceeds even after the start-up of the cooling. Further, the valley of the temperature swing and the secondary nucleation (peak of the number of particles) are not consistent. This is presumably because there is a waiting time for the secondary nucleation and the detection was conducted 10 minutes after the termination of the cooling (50° C.). It is observed that by the repeated temperature swing the ratio of crystals having a particle size of 100 μm or less was decreased and the peak of the large particle size grew.

Figure 7A:
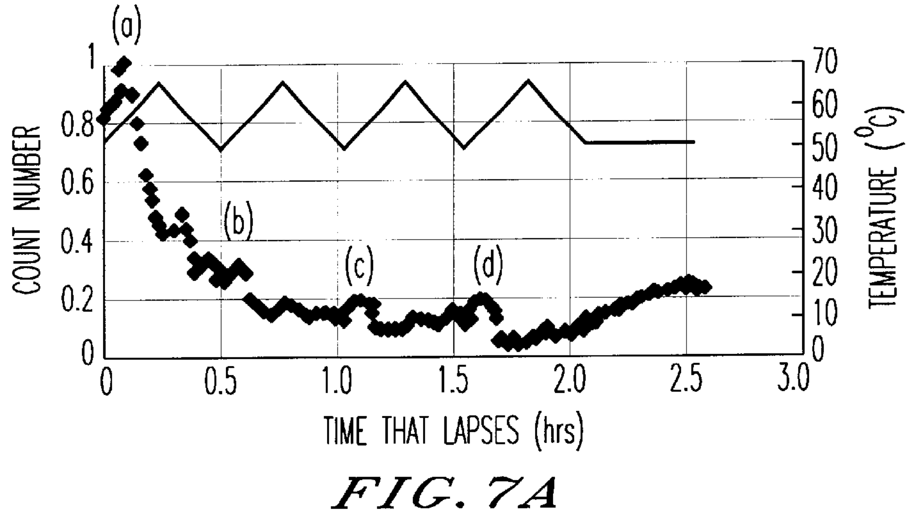
FIG. 7A indicates the change in the number of particles with time under the No. 2 condition (Experiment Example 1).
Figure 7B:
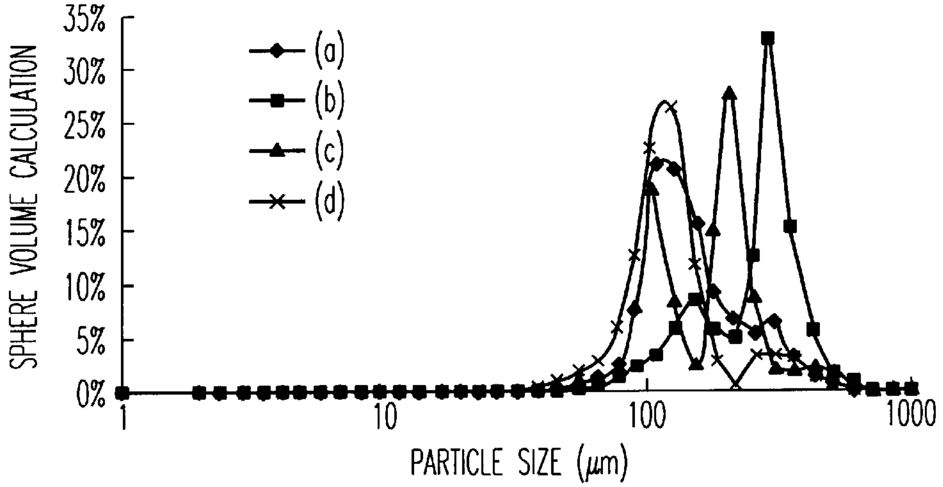
FIG. 7B indicates the change in the particle size distribution with time under the No. 2 condition (Experiment Example 1).

(b) Temperature pattern No. 2:

In the condition No. 2 shown in FIG. 7A, the secondary nucleation occurred immediately after the cooling in comparison with the condition No. 1 shown in FIG. 6A. That is, the secondary nucleation occurred earlier. This is presumably because ΔC in the condition No. 2 is larger than that in the condition No. 1 so that excessive dissolution is reached earlier during the cooling (refer to FIG. 8). After the fourth cooling, the mass was maintained at 50° C. During that time, the count number was continuously increased. This is presumably because there is the waiting time for the nucleation as mentioned under (a) concerning the condition No. 1.

Figure 8:
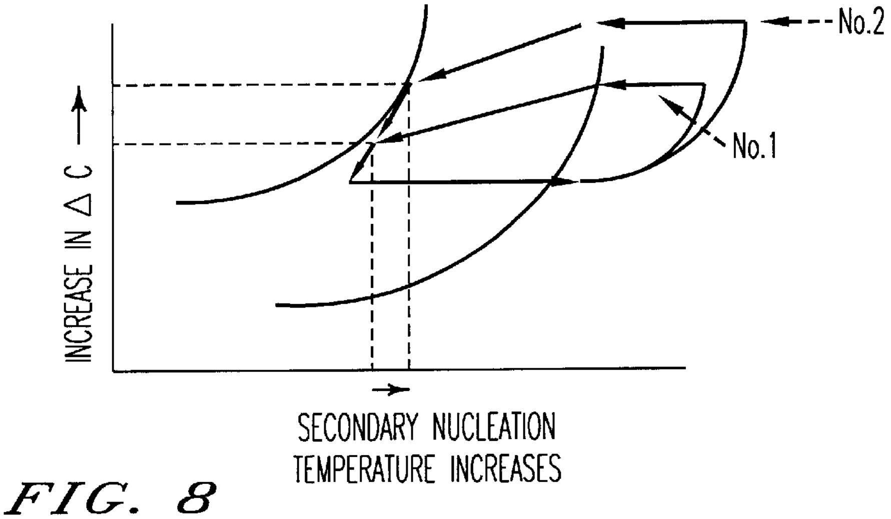
FIG. 8 indicates the difference in the temperature amplitude and the secondary nucleation temperature (Experiment Example 1).

In comparison with the condition No. 1 shown in FIG. 6B, the ratio of fine crystals having a particle size of approximately 100 μm was not decreased so much even by repeating the temperature swing. This is presumably because, as shown in FIG. 8, the amplitude of the temperature swing is increased to increase the degree of supersaturation in the secondary nucleation and also increase the amount of the secondary nucleation.

(c) Temperature pattern No. 33

Figure 9A:
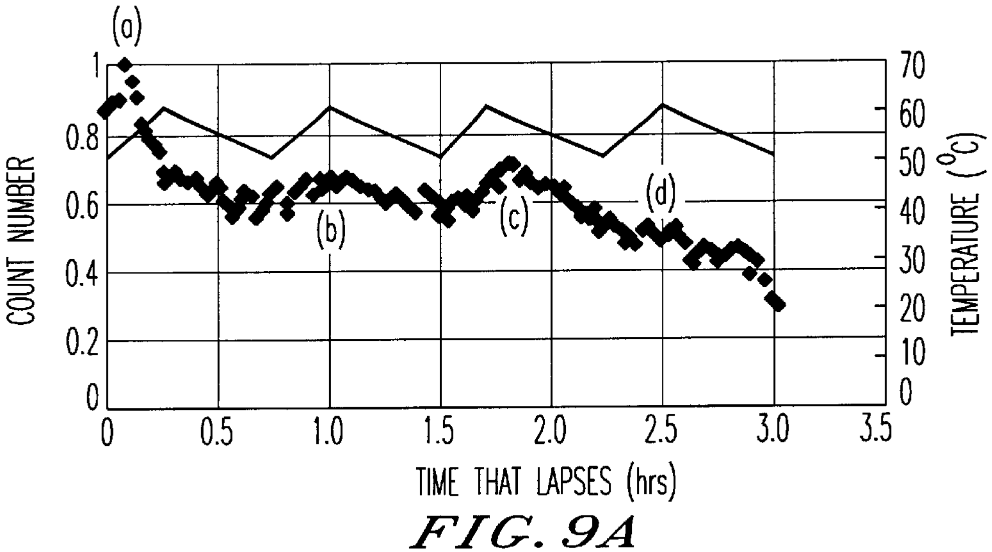
FIG. 9A indicates the change in the number of particles with time under the No. 3 condition (Experiment Example 1).

In the condition No. 3 shown in FIG. 9A, the temperature swing amplitude is the same as that in the condition No. 1. However, the increase in the count number that indicates the secondary nucleation starts relative to the valley of the cooling (near the termination of the cooling) in comparison with the condition No. 1. This is considered to prove that there is the waiting time for the nucleation, as already stated. Or, the apparent excessive solubility is considered to be decreased with the decrease in the cooling rate. On the other hand, the increase in the cooling rate leads to the decrease in the period of time for maintaining the slurry in a metastable region, namely in a stable crystal growth state. Thus, it is considered that there is an optimum cooling rate depending on properties of matter and crystallization conditions.

Figure 9B:
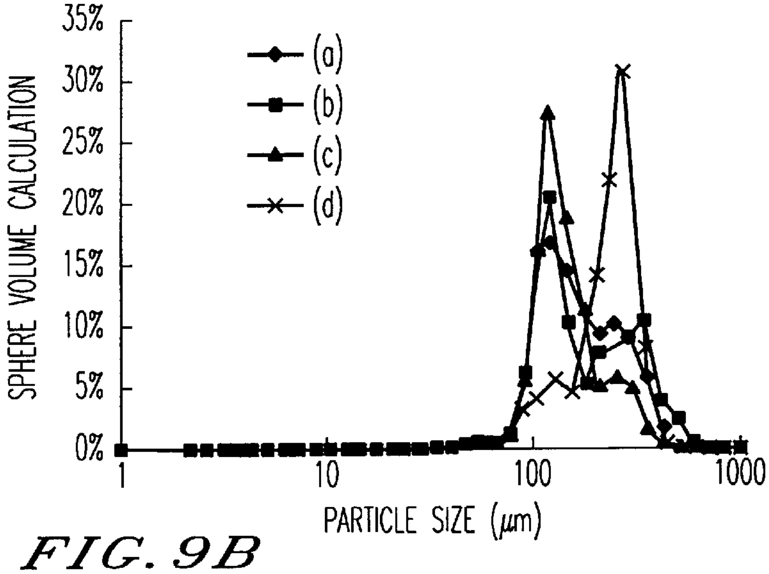
FIG. 9B indicates the change in the particle size distribution with time under the No. 3 condition (Experiment Example 1).

As shown in FIG. 9B, the cooling rate is lower and the rate of the secondary nucleation is higher than in the condition No. 1, so that the fine crystals having a particle size of approximately 100 μm is not so decreased in number. At the point of time (d) in FIG. 9A, the count number indicating the secondary nucleation is little increased, so that the ratio of fine crystals is decreased.

(d) Temperature patterns Nos. 4 and 5:

The change in the number of particles with time and the change in the particle size distribution with time under such control conditions that the temperature was constantly set at 50° C. or 60° C. are shown in FIG. 10A to FIG. 11B.

With respect to the change in the number of particles, the figures reveal that it tends to increase under the condition No. 4, and it tends to decrease under the condition No. 5. It tends to increase under the condition No. 4 because, as shown in the experiment flow sheet (FIG. 4), the temperature was once increased to 60° C. as the pretreatment so that the supersaturated state still continues even after the cooling to 50° C. It tends to decrease under the condition No. 5 because, in spite of the starting slurry being charged at 60° C., the saturation concentration is not reached and the dissolution gradually proceeds.

Figure 10A:
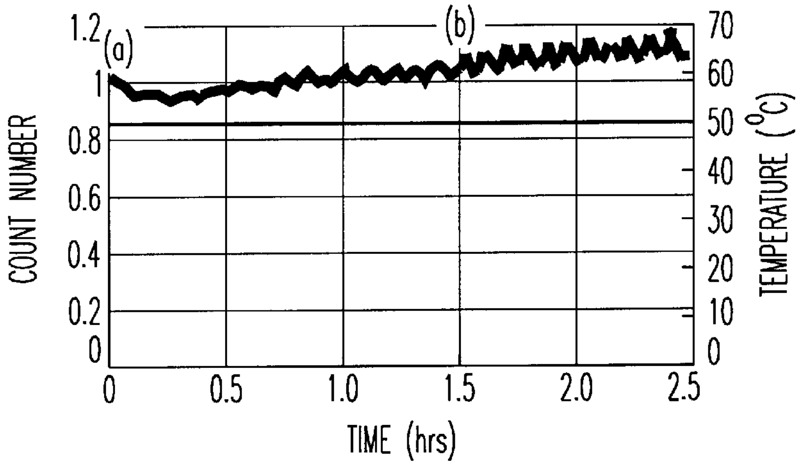
FIG. 10A indicates the change in the number of particles with time under the No. 4 condition (Experiment Example 1).
Figure 10B:
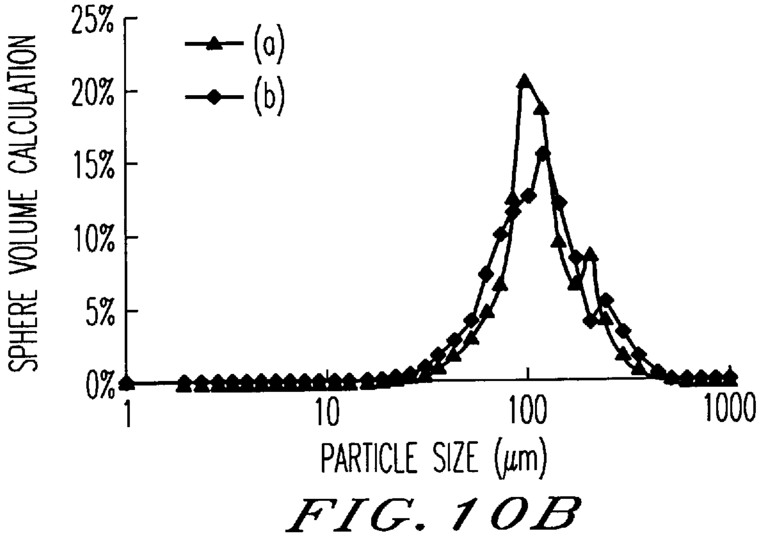
FIG. 10B indicates the change in the particle size distribution with time under the No. 4 condition (Experiment Example 1).
Figure 11A:
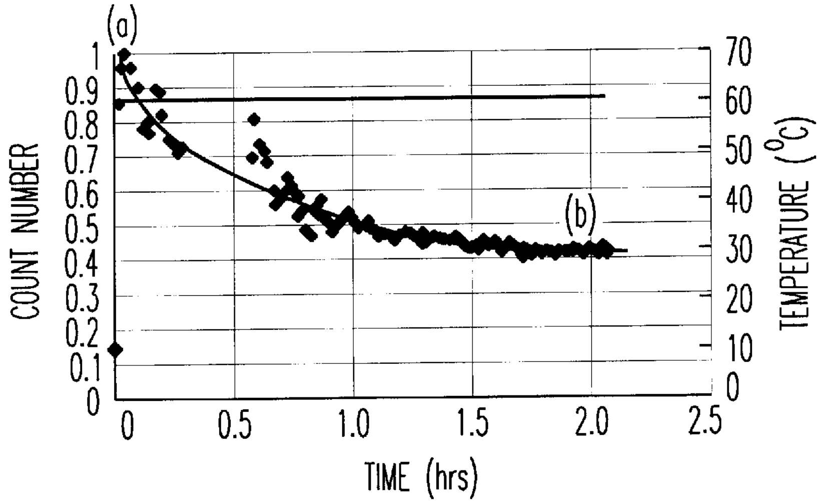
FIG. 11A indicates the change in the number of particles with time under the No. 5 condition (Experiment Example 1).
Figure 11B:
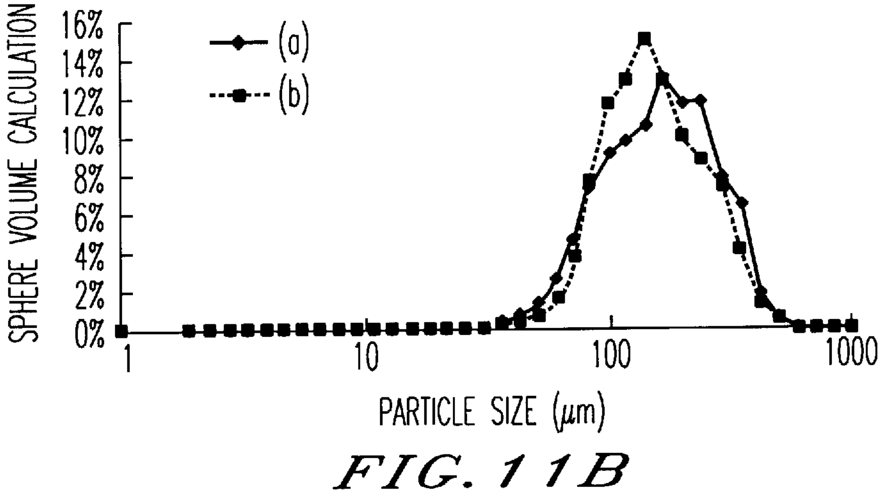
FIG. 11B indicates the change in the particle size distribution with time under the No. 5 condition (Experiment Example 1).

As is apparent from FIGS. 10B and 11B, the particle size distribution was little changed with time in these cases.

Figure 12:
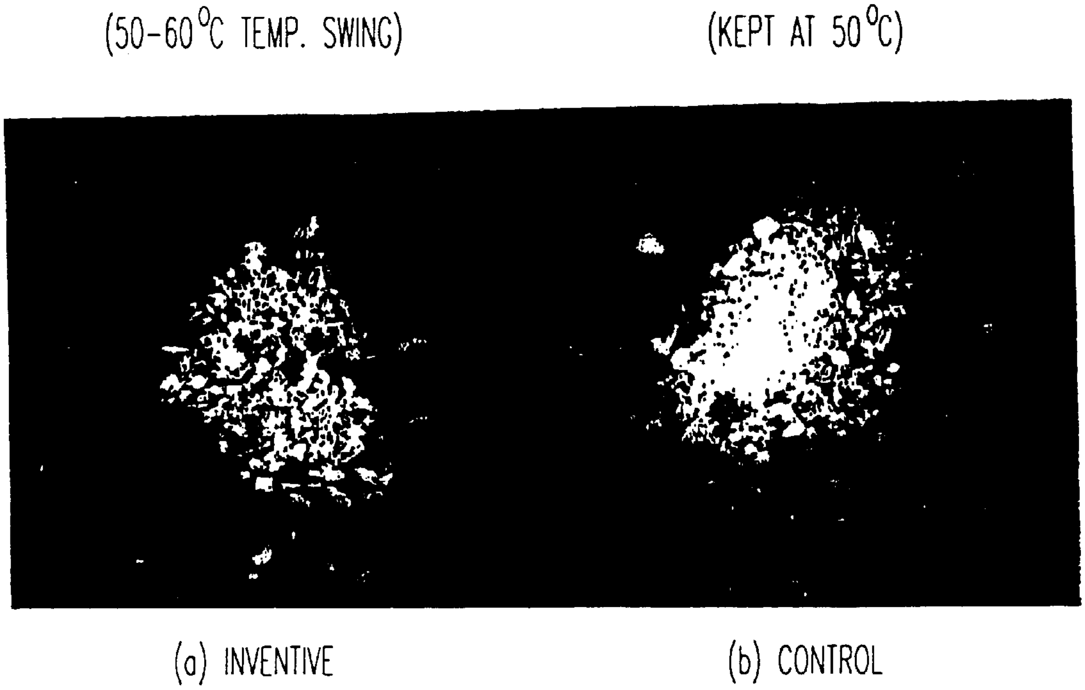
FIG. 12 indicates photos (×1) of the crystals (Experiment Example 1).

(e) Photos of crystals:

Photos (×1) of crystals obtained by subjecting the slurries after the completion of the experiment under the conditions Nos. 1 and 4 to solid-liquid separation with a solid-liquid separator and conducting the drying are shown in FIG. 12. In comparison with the particle size of the crystals (control) obtained under the condition No. 4 in which the temperature was maintained at 50° C., the particle size of the crystals (present invention) obtained through the temperature swing is much increased.

(4) Summary of the experiment:

Arg.HCl crystals were suspended in a saturated solution, and the temperature-swung procedure was conducted, making it possible to decrease the fine crystals and increase the particle size of the crystals.

The effects of the temperature-swung method are influenced by the nucleation waiting time, the crystal dissolution rate, ΔC (amount of crystals dissolved), the occurrence of the secondary nucleation (amount and rate), the crystal growth rate, and the like. These are determined from the material properties of substances to be crystallized, the crystallization conditions, the characteristics of the equipment, and the like. The parameters (amplitude and period) of the temperature-swung method can be determined, in consideration of such factors, as required.

Example 1

Arg.HCl was purified by the crystallization method with the particle size distribution being controlled in accordance with the present invention.

(1) For the convenience of explanation, the conventional vacuum concentration crystallization will be first described. That is, as a vacuum concentrator, an existing vacuum concentrator having a capacity of approximately 25 kiloliters was used. The concentration was conducted by the fed-batch method. During the concentration, 260 g/liter of an Arg.HCl solution was fed in such manner that the amount of the slurry solution was maintained at a level of 6.5 kiloliters. As a condenser, a barometric condenser was used.

(2) The crystallization method of the present invention was practiced by repeating such a conventional method without changing the concentration time and the like except that the temperature swing was added as the concentration condition. The temperature control for the temperature swing was conducted by adjusting the degree of vacuum, provided that the amount of the water vapor (steam) was approximately 2 t/hr before introduction of the seed crystals and reduced to approximately 1.3 t/hr after the introduction of the seed crystals. In this case, the rate of the increase in the concentration was approximately 50 g/liter·hr. In order to realize the effects of the temperature-swung method, the rate of the increase in the concentration by the temperature rise of the temperature swing has to exceed 50 g/liter·hr (refer to the principle of the temperature-swung method described above). After the feeding was completed, the temperature was raised to 60° C., and the concentration was terminated.

In order to confirm the effects of the present invention compared to those of the conventional method in practicing the conventional method and the crystallization method of the present invention, the relationship of the temperature pattern and the liquid concentration of the slurry during the concentration crystallization and the particle size distribution of the resulting product crystals was examined.

The temperature pattern and the change in the temperature were examined upon installing an in-line refractometer supplied by K-PATENTS in the concentrator. As an index of the concentration, the refractive index (Brix) was used. The Arg.HCl concentration (10 g/liter)=Brix (50° C.)×0.98. The change in the Brix value at 50° C. and 60° C. was also measured, and the difference was only approximately 1%.

With respect to the crystal particle size distribution, the crystals were separated from the slurry with a siphon peeler, and dried with a conical drier. Then, the crystal size distribution was measured before sieving, using a ROBOT SHIFTER supplied by Seishin Kigyo. Each plot in FIG. 14 indicates a ratio of the weight on the sieve corresponding to each particle size to the total weight.

A total of 5 lots of crystallizations (Lots (1) to (5)) including the concentration crystallization according to the conventional method and the concentration crystallization according to the present inventive method were conducted.

Figure 13A:
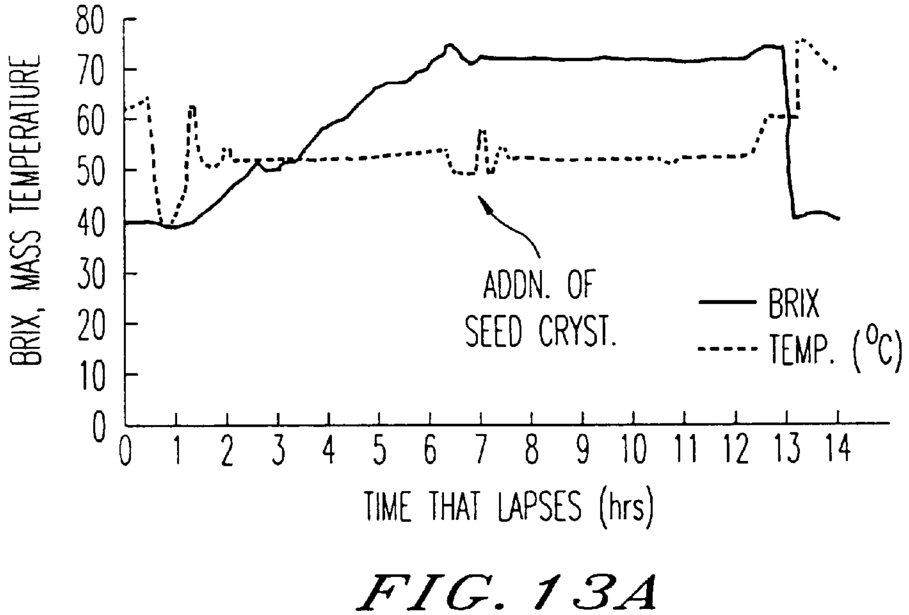
FIG. 13A indicates a temperature pattern in concentration crystallization (Example 1).
Figure 13B:
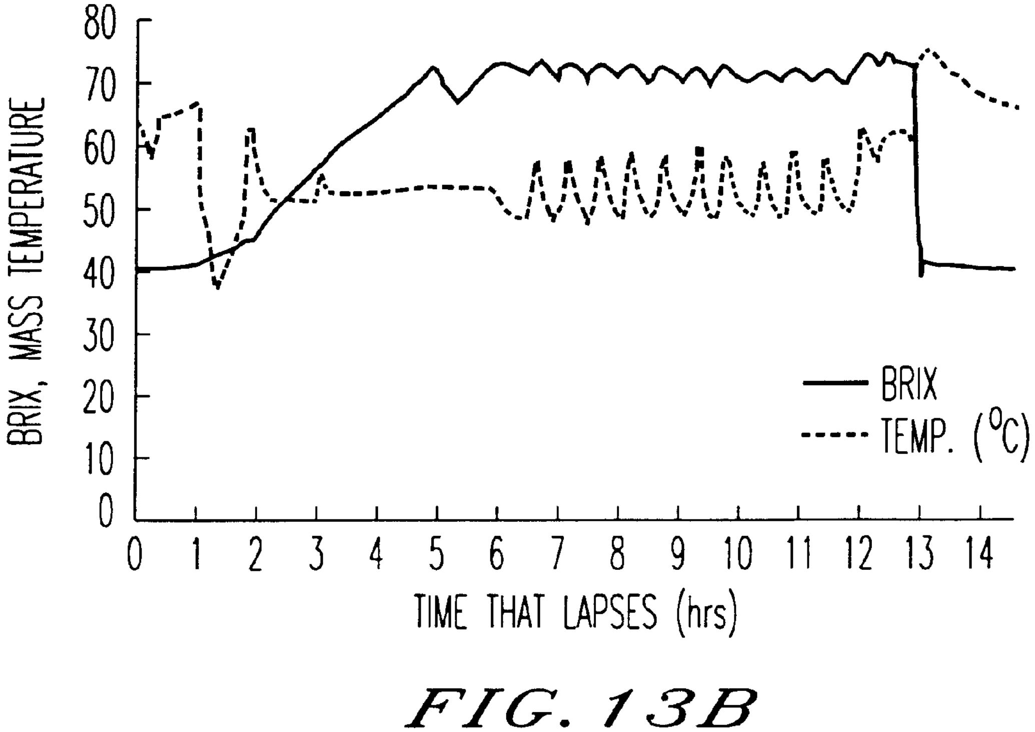
FIG. 13B indicates a temperature pattern in concentration crystallization (Example 1).
Figure 13C:
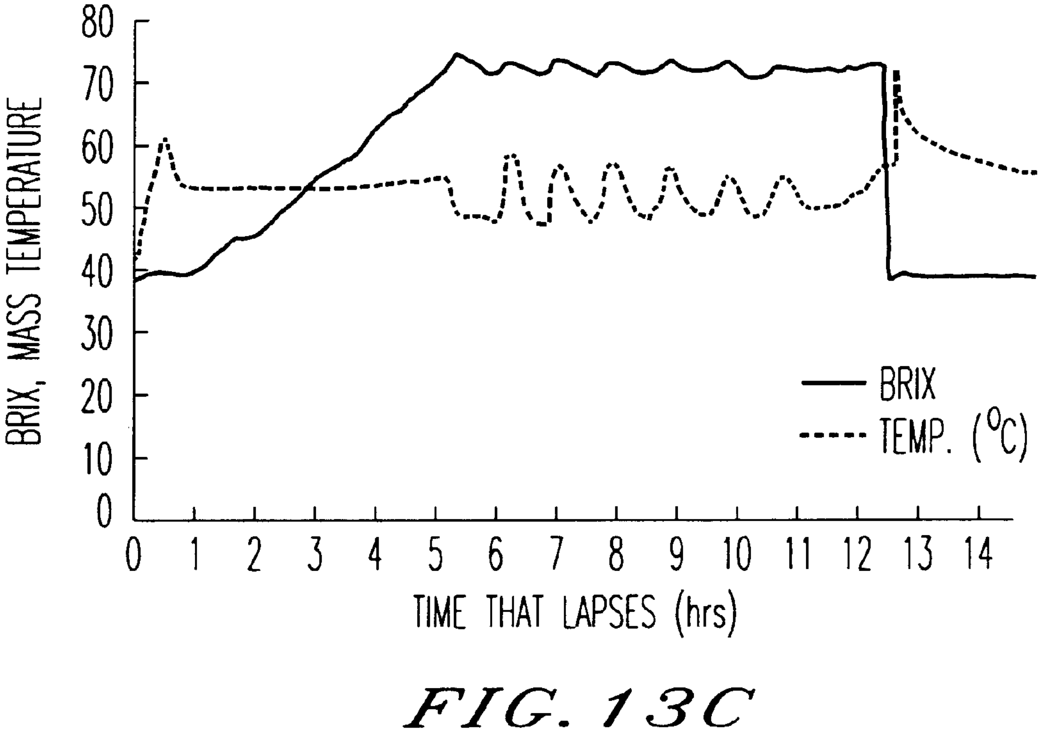
FIG. 13C indicates a temperature pattern in concentration crystallization (Example 1).
Figure 13D:
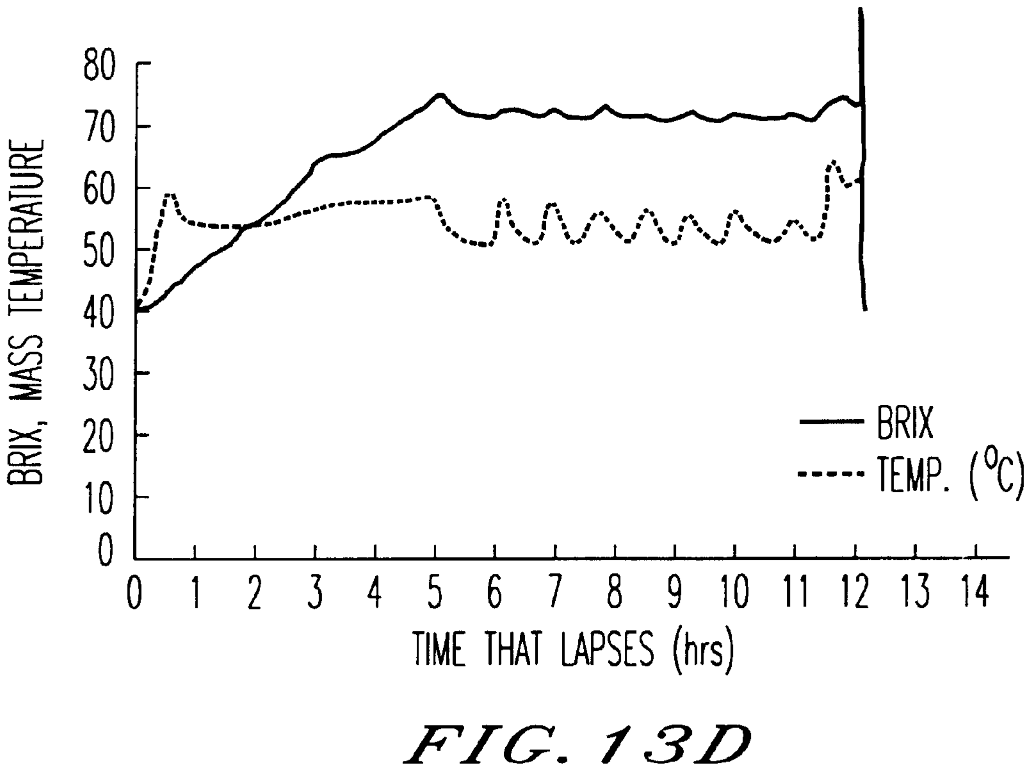
FIG. 13D indicates a temperature pattern in concentration crystallization (Example 1).
Figure 13E:
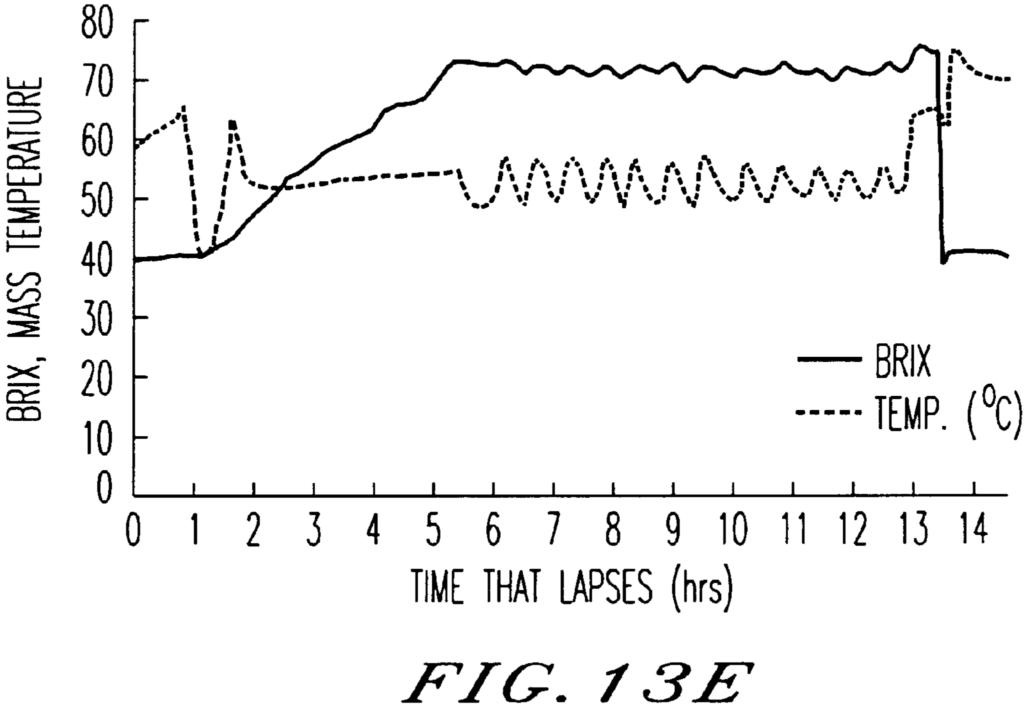
FIG. 13E indicates a temperature pattern in concentration crystallization (Example 1).
Figure 14:
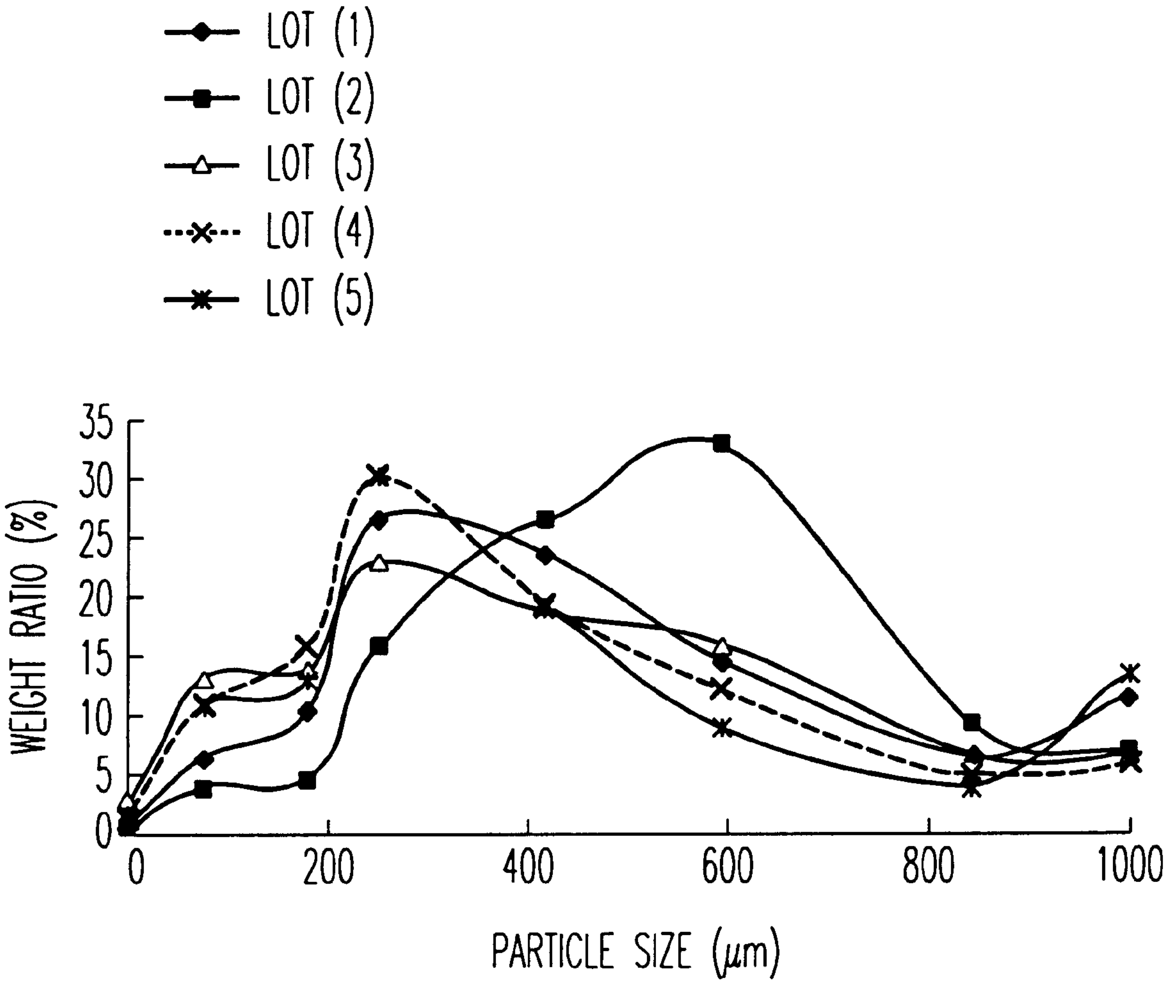
FIG. 14 indicates the particle size distribution of a product.
Figure 15A:
FIG. 15 indicates photos (×26) of the crystals (Example
Figure 15B:
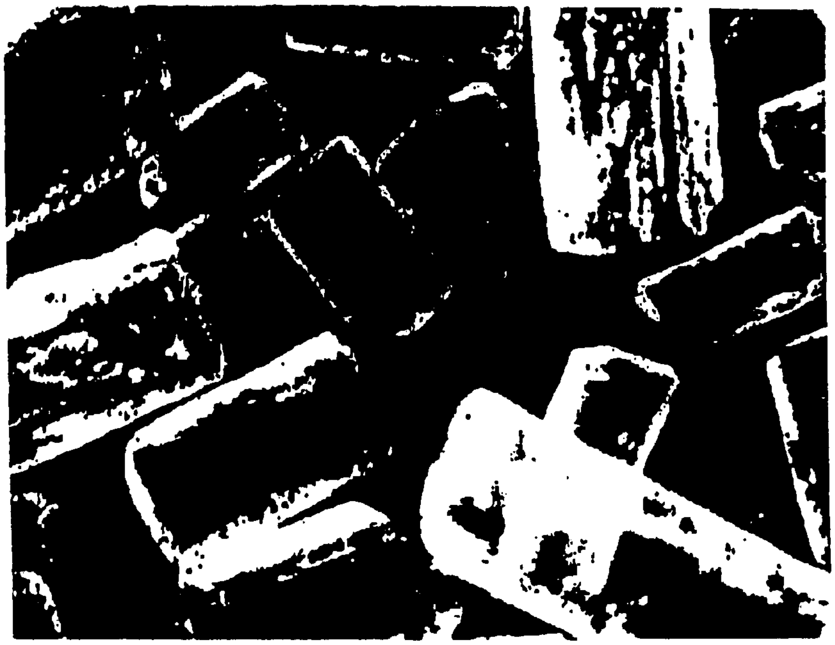

The temperature patterns in the 5 lots are shown in FIGS. 13A to 13E, and the crystal particle size distributions in these lots, in FIG. 14. In each lot, it is identified that the Brix is increased with the increase in the concentration by the concentration and is decreased in a while after the addition of seed crystals owing to crystallization. Photos (×26) of the crystals in Lot (1) (conventional method) and Lot (2) (inventive method) are shown in FIG. 15.

To add to this, Lot (1) in FIG. 13A is one according to the conventional method in which the temperature swing was not conducted. The particle size distribution has a typical pattern according to the conventional method in which there are peaks near 100 $\mu$m and near 120 $\mu$m. The ratio of the crystals having a particle size of approximately 100 $\mu$m reaches as high as approximately 10%.

In Lot (2) in FIG. 13B, the ratio of the crystals having a particle size of approximately 100 $\mu$m is as low as approximately 3%. The particle size is large as a whole, and the effects of the temperature swing is high. Thus, This is a lot of the present invention. The temperature pattern of this lot was between 49 and 58° C. ($\Delta$T=9° C.), and the period thereof was approximately 30 minutes. The initial concentration amplitude was 20 g/liter, and the rate of the increase in the concentration by the temperature rise was 80g/liter·hr. Since the increase in the concentration by the concentration was 50 g/liter·hr, the above-mentioned value was to exceed this.

Lot (3) in FIG. 13C was similar to Lot (2) for several hours after the crystallization. However, for the latter half thereof, the amplitude of the temperature swing was smaller, and the period was increased. Thus, Lot (3) did not give such remarkable effects as Lot (2). From this fact, it is considered that the secondary nucleation occurred in the latter half of the concentration.

Between Lot (4) in FIG. 13D and Lot (5) in FIG. 13E, there was seen almost no change in the particle size distribution. This is presumably because the period was greater in Lot (4) and the amplitude was smaller in Lot (5), so that the rate of the increase in the concentration in the temperature rise was less than the rate of the increase in the concentration by the concentration and fine crystals little disappeared.

The photos in FIG. 15 reveals that almost no fine crystals are present in Lot (2) and the particle size is increased, owing to the temperature swing.

From such results, it can be identified that the temperature-swung method of the present invention enables the particle size of the crystals to be adjusted only by adding the temperature swing to the ordinary concentration procedure without the change in the concentration conditions such as the concentration time and the like in the conventional method whereby it is, in turn, possible to decrease the ratio of fine crystals and increase the particle size. In the temperature swing with an amplitude of from 48 to 59° C. and a period of 30 minutes among the conditions employed in this Example, the ratio of fine crystals was lowest, and the particle size of crystals was largest. The ratio of the fine crystals under the sieve was reduced to as low as 3%. As is apparent from the results in Lots (2) to (5), the effects of the temperature-swung method are influenced by the amplitude, the period of the temperature swing and the like. Thus, it is necessary to appropriately select these. Further, in order to obtain the effects of the temperature-swung method, the rate of the increase in the concentration at the time of the temperature rise has to exceed the rate of the increase in the concentration by the concentration.

When the concentration crystallization was conducted according to this Example except that L-lysine acetate (Lys.AcOH) was used instead of the Arg.HCl, the same effects by controlling the particle size distribution could be provided. In this case, a surface condenser was used as a condenser.

In accordance with the present invention, as has been described above, the crystallization by controlling the particle size distribution (i.e., with the particle size distribution being controlled) can be conducted in a simple vacuum concentrator upon only adding the temperature swing to the temperature control without the need for an additional equipment and without the change in the procedure conditions such as the prolongation of the concentration time. Thus, it finds quite wide application, and is practical.

What is claimed as new and desired to be secured by Letters Patent is:

1. A method of controlling the particle size distribution of crystals by crystallization, comprising:

precipitating crystals from a slurry by vacuum concentration crystallization, and periodically varying the temperature of said slurry upwards and downwards within a fixed temperature range during said vacuum crystallization concentration; wherein said temperature is varied by adjusting the pressure in said vacuum concentration crystallization.

2. The method of claim 1, wherein prior to said precipitating, said slurry comprises at least a mother, liquor.

3. The method of claim 1, wherein said crystals comprise a salt of at least one selected from the group consisting of L-arginine and L-lysine.

4. The method of claim 3, wherein said salt is selected from the group consisting of L-arginine hydrochloride and L-lysine acetate.

5. The method of claim 1, wherein said fixed temperature range comprises a lower temperature greater than or equal to 50° C. and an upper temperature less than or equal to 60° C.; wherein said lower temperature is lower than said upper temperature.

6. The method of claim 1, wherein said fixed temperature range comprises a lower temperature greater than or equal to 50° C. and an upper temperature less than or equal to 65° C.; wherein said lower temperature is lower than said upper temperature.

7. The method of claim 1, wherein said fixed temperature range comprises a lower temperature of 50° C. and an upper temperature of 60° C.

8. The method of claim 1, wherein said fixed temperature range comprises a lower temperature of 50° C. and an upper temperature of 65° C.

9. The method of claim 1, wherein said fixed temperature range is a range, ΔT, from 9 to 15° C.

10. The method of claim 1, wherein said periodically varying comprises a periodic time of 30 minutes.

11. The method of claim 1, wherein said temperature is the mass temperature.

12. The method of claim 1, further comprising separating and drying said crystals.

13. The method of claim 1, wherein approximately 3% of said crystals have a particle size of approximately 100 μm.

14. The method of claim 1, wherein said slurry comprises a mother liquor solution, wherein said vacuum concentration crystallization causes a first rate of increase in the concentration of said solution, wherein said varying of said slurry temperature upwards causes a second rate of increase in the concentration of said solution, and wherein the second rate of increase is greater than the first rate of increase.

15. The method of claim 1, wherein said vacuum concentration crystallization is carried out in a continuous manner, a batch manner, or a fed-batch manner.

* * * * *